United States Patent
Fiolitakis

[11] Patent Number: 5,808,128
[45] Date of Patent: Sep. 15, 1998

[54] METHOD OF MANUFACTURING VINYLTRICHLOROSILANE

[75] Inventor: Emmanuel Fiolitakis, Duelmen, Germany

[73] Assignee: Huels Aktiengesellschaft, Marl, Germany

[21] Appl. No.: 950,440

[22] Filed: Oct. 15, 1997

[30] Foreign Application Priority Data

Nov. 6, 1996 [DE] Germany .......................... 196 45 700.9
Jun. 28, 1997 [DE] Germany .......................... 197 27 576.1

[51] Int. Cl.$^6$ ....................................................... C07F 7/14
[52] U.S. Cl. ............................................................... 556/481
[58] Field of Search ................................................ 556/481

[56] References Cited

U.S. PATENT DOCUMENTS

| | | | |
|---|---|---|---|
| 2,770,634 | 11/1956 | Weyenberg | 556/481 |
| 3,666,782 | 5/1972 | Mui et al. | 556/481 |
| 3,706,776 | 12/1972 | Seiler et al. | 556/481 |
| 5,075,480 | 12/1991 | Hange et al. | 556/481 |
| 5,344,950 | 9/1994 | Hange et al. | 556/481 |

*Primary Examiner*—Paul F. Shaver
*Attorney, Agent, or Firm*—Oblon, Spivak, McClelland, Maier & Neustadt, P.C.

[57] ABSTRACT

The invention relates to a method of manufacturing vinyltrichlorosilane by reacting vinyl chloride with trichlorosilane, at elevated temperature. The reaction is carried out at 400°–850° C., preferably 550°–800° C., in a fluidized bed.

8 Claims, 2 Drawing Sheets

METHOD OF MANUFACTURING VINYLTRICHLOROSILANE

BACKGROUND OF THE INVENTION

1. Field of the Invention

The invention relates to a continuous method of manufacturing vinyltrichlorosilane by reacting vinyl chloride with trichlorosilane (the latter also being known as "silicochloroform").

2. Discussion of the Background

Vinyltrichlorosilane is an important starting material for manufacturing a number of valuable functionalized organosilane. For example, vinylalkoxysilanes are derived from vinyltrichlorosilane, and in turn are used for, inter alia, the silane coating of polyethylene.

In E.P. 0,438,666 B1 and E.P. 0,456,901 B1, both incorporated herein by reference, the principles for the design and operation of ring-gap reactors containing axially symmetrically disposed rotating expulsion bodies are described. Such reactors enable industrial-scale manufacture of vinyltrichlorosilane by reaction of trichlorosilane and vinyl chloride, at elevated temperature, corresponding to the equation:

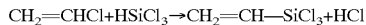

$$CH_2=CHCl + HSiCl_3 \rightarrow CH_2=CH-SiCl_3 + HCl$$

It has been found to be advantageous to use a substantial excess of trichlorosilane in this conversion (e.g., a ratio of trichlorosilane to vinyl chloride of in the range of 4:1 to 6:1 by weight, corresponding to a stoichiometric ratio of c. 2:1 to 3:1). However, this method provides a selectivity for vinyltrichiorosilane of only about 70% (with reference to the vinyl chloride converted). In addition to the desired vinyltrichlorosilane, one obtains varying amounts of tetrachlorosilane and ethyltrichlorosilane, as well as various other high- and low-boiling substances. In the ring-gap reactor, the components of the reaction mixture are heated rapidly to the reaction temperature in a very short pre-heat zone, thereby enabling improved utilization of the reaction space, and a nearly adiabatic reaction. However, the ring-gap method promotes spontaneous decomposition reactions wherein silicon and carbon are deposited in the form of a black powder. Thus, the method is susceptible to problems and failures, in addition to being difficult to control safely.

OBJECTS OF THE INVENTION

The underlying problem solved by the present invention is to devise an economical method of manufacturing vinyltrichlorosilane by reacting vinyl chloride with of trichlorosilane, which provides improved yields, is easy to regulate, safe to operate, and not susceptible to problems and failures.

SUMMARY OF THE INVENTION

It was found, surprisingly, in connection with the present invention which solves said underlying problem, that vinyltrichlorosilane can be produced advantageously at elevated temperature by reacting vinyl chloride with trichlorosilane if the reaction is carried out at 400°–850° C., including 450°, 500°, 550°, 600°, 650°, 700°, 750° and 800° C., in a fluidized bed.

DETAILED DESCRIPTION OF THE INVENTION

Figure 1:
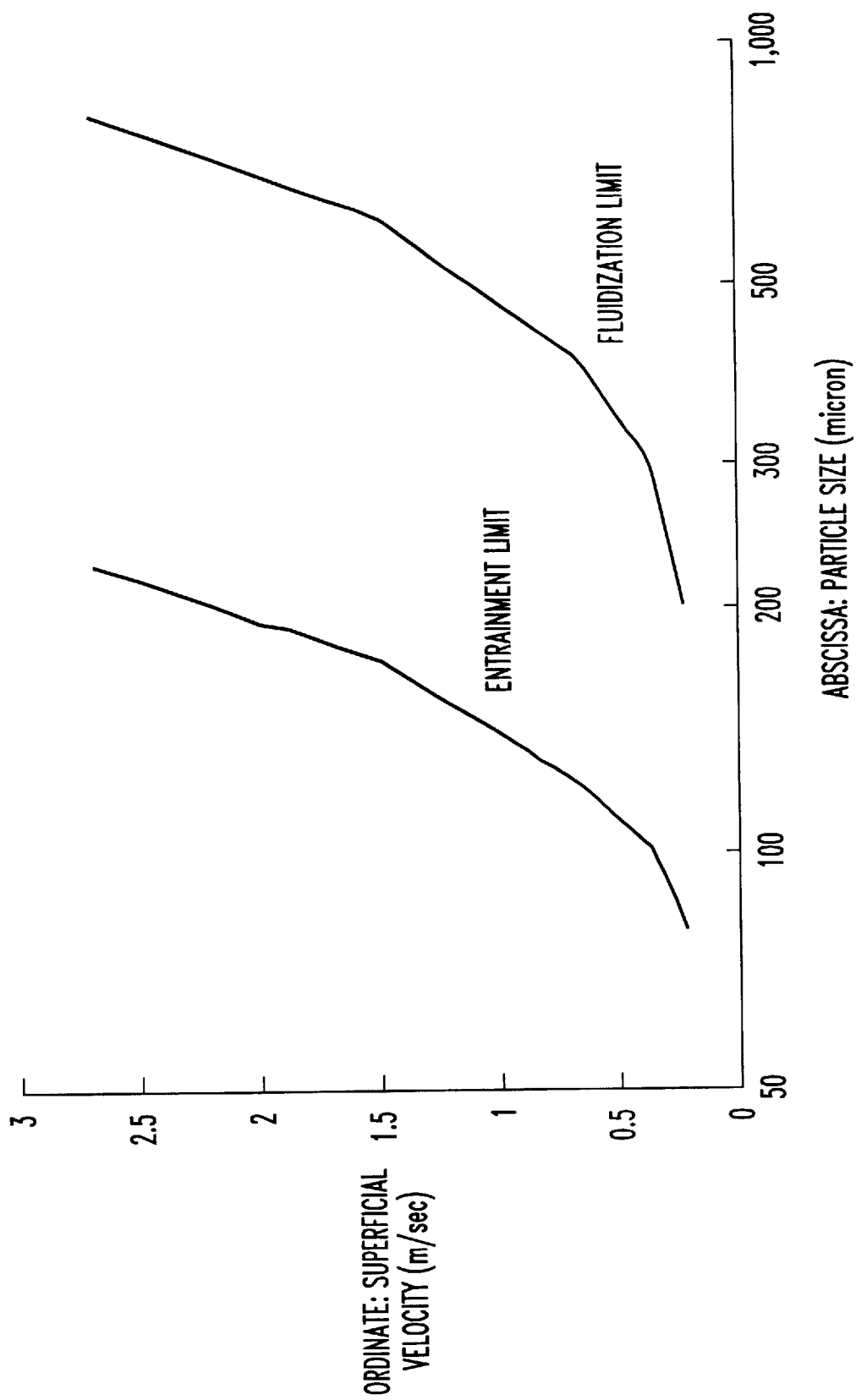
FIG. 1 shows a graph of fluidized bed material particle size versus superficial gas velocity.

The inventive method produces vinyltrichlorosilane at conversions (with reference to the vinyl chloride) of up to about 50%, including above 25, above 30, above 35, above 40, and above 45% with selectivities of up to 90% including above 75%, above 80%, and above 85%,. The selectivities obtained are, surprisingly, better than those of the known method carried out in a ring-gap reactor. Certainly the compelling expectation was that in a fluidized bed there would be a much greater degree of formation of high-boiling oligomers of vinyltrichlorosilane, and thereby lower selectivity, because of the higher degree of back-mixing compared to the ring-gap method. In addition to improved selectivity, the inventive method provides good space-time yields at a relatively low excess of trichlorosilane, compared to the method carried out in a ring-gap reactor. The inventive method may be operated at steady state over a relatively long period without problems, with practically no intervention. The undesirable deposition of carbon black and silicon is essentially eliminated.

Technical grade vinyl chloride with a purity of 99.95–99.99% may be used for the invention method. This material is produced in large scale, e.g. by the dehydrohalogenation of 1,2-dichloroethane. The trichloarosilane used may have a purity of 96.0–99.0, e.g. may be a material produced from silicon and chlorine, or silicon and hydrogen chloride; such trichlorosilane contains, inter alia, small amounts of dichloro- and tetrachlorosilane. The two starting materials may be used in stoichiometric amounts or with an excess of trichlorosilane, e.g. up to a molar ratio of 3:1 (corresponding to a weight ratio of about 6:1 including 2:1–4:1) including 1.5:1, 2:1 and 2.5:1.

Advantageously, the reaction temperature in the fluidized bed is 550°–800° C. As a rule, atmospheric pressure is used. The mean residence time of the flow of materials in the fluidized bed depends basically on the temperature in the bed but also depends on a number of other process parameters known to those of skilled in the art. In general, the residence time is 0.1–0.2 sec. Thus, the inventive method is distinguished by its high space-time yields. The optimum residence time for (different process conditions other than those described here can be readily determined by routine preliminary experimentation by one of ordinary skill.

The material(s) used for the fluidized bed may be any inorganic particulate material(s) of suitable particle size which is are solid and inert toward the starting materials and vinyltrichlorosilane, under the given process conditions. Suitable materials are, e.g., silicon nitride and, particularly, silicon carbide. Advantageously, the inert fluidized bed material has a particle size in the range of 80–800 micron, preferably 200–800 micron, including 300, 400, 500, 600 and 700 micron, with a preferred mean particle diameter of 400–600 micron, preferably 450–550 micron. The thickness of the bed layer at rest is generally in the range of a few centimeters to 30 cm, depending on the capacity of the apparatus.

The optimum particle size distribution for the inert fluidized bed material depends on the reactor geometry and on the reactor loading, i.e. the throughput of the reactor. FIG. 1 presents the calculated particle size limits for the fluidized bed as a function of the flow speed on a hollow cylinder basis (so-called "superficial velocity"). The left curve represents the limit below which fine particles are lifted out of the fluidized bed (entrained), under the reaction conditions and for the given special velocities; and above which limit fine particles are not entrained. The right curve represents the limit above which particles in the somewhat large size range are no longer brought into fluidization; and below which particles in the somewhat large size range are still fluidizable.

Advantageously, the starting materials, comprising vinyl chloride, which is gaseous at room temperature and atmospheric pressure, and trichlorosilane, which boils at 31.8° C., are introduced in vapor form preferably from below, into a heated fluidized bed. The height of a suitable fluidized bed is generally in the range of 3 to 8 times the height of the bed at rest. Under some conditions the amount of flow of vaporous starting mixture introduced will not suffice to suitably fluidize the bed. Accordingly, advantageously an inert gas such as nitrogen is introduced together with the vaporous starting materials or in a separate introduction, with such introduction being, again, preferably from below. The inert gas may be pre-heated. The optimum amount of inert gas can be readily determined by preliminary experiments; generally the amount is 0.4–1.2 mol/mol vinyl chloride.

Figure 2:
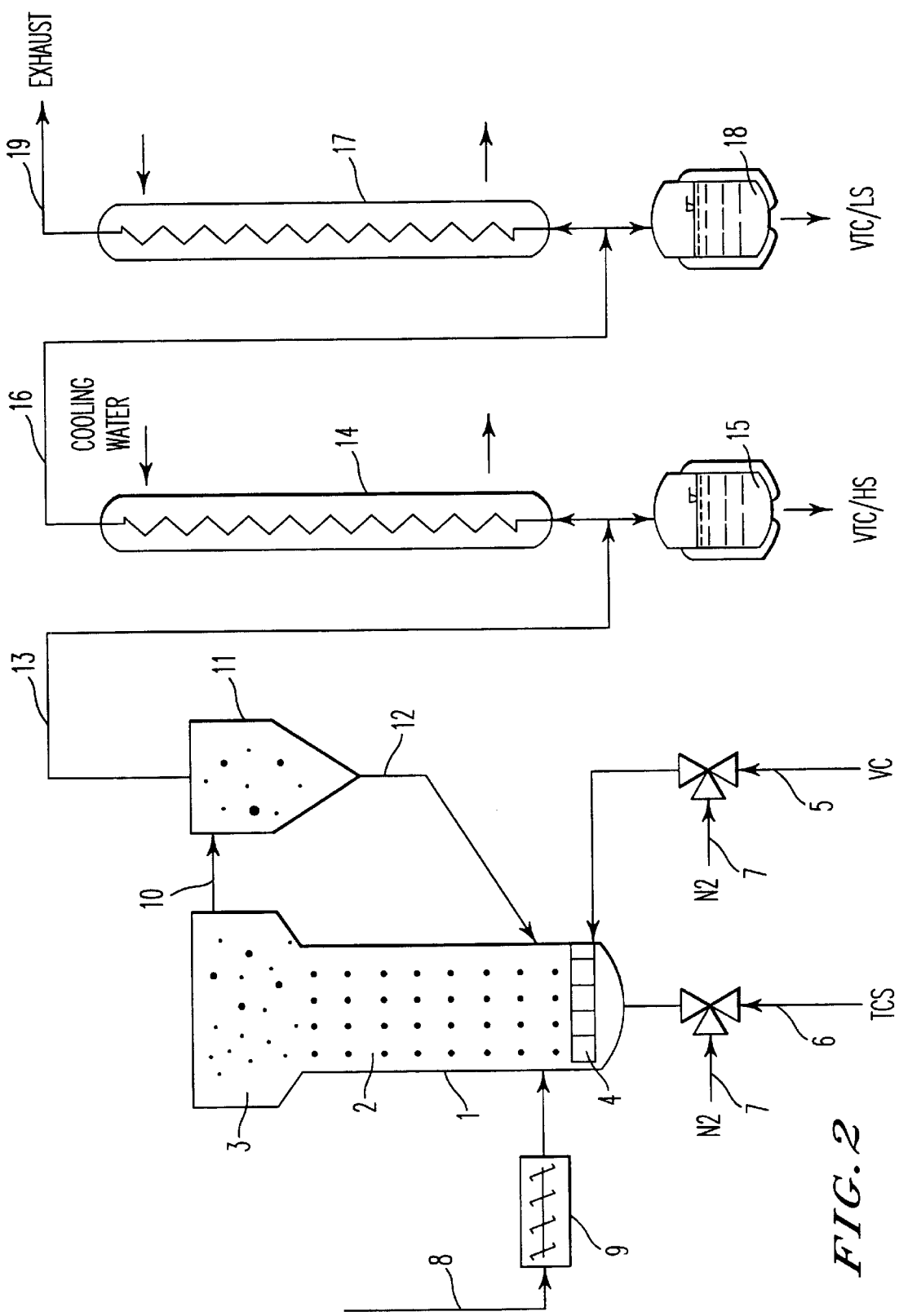
FIG. 2 shows an apparatus for carrying out the invention method.

An apparatus for carrying out the inventive method is shown schematically in FIG. 2. Reactor 1 is a vertical vessel with a cylindrical cross section, widened in its upper region to facilitate separation of the larger-size particles 2 of the inert fluidized bed material from the smaller-size particles 3 of said material. In the widened region, the flow speed of the gaseous reaction mixture is reduced, and consequently the amount of entrained particles of fluidized bed material is reduced. When at rest, the layer of particles of fluidized bed material rests on a sieve plate or wire screen 4, at the lower end of the reactor 1. The pore diameter (mesh) of the plate or screen is less than the mean diameter of the particles of the fluidized bed material, and preferably is less than the diameter of the smallest particles of the fluidized bed material. Advantageously, the reactor is heated by spiral electric heating elements, and is equipped with the usual means of regulating temperature. The starting materials, VC (vinyl chloride) 5 and TCS (trichlorosilane) 6 are introduced to the reactor 1 in vapor form, at a location or locations below the sieve plate of wire screen 4. The starting materials may be intermixed with nitrogen 7. To compensate for the entrained fluidized bed material which is carried away, fresh doses 8 are added to the fluidized bed via a mechanical conveyor 9, or by pneumatic conveyance with the use of an inert gas stream bearing fluidized bed material. (Pneumatic means not shown.)

The stream 10 leaving the upper part of the reactor, which stream is comprised of gaseous raw product and entrained fluidized bed material, is passed into a cyclone separator 11 where most of the entrained fluidized bed material is removed from the gaseous raw product. The fluidized bed material which is separated out is returned to the reactor 1 via return line 12, at a point slightly above the sieve plate or wire screen 4. The gaseous raw product in line 13 may still contain appreciable amounts of fine solids. This product stream is passed to a water-cooled cooling unit 14 where it is separated into a high-boiling fraction 15, containing most of the vinyltrichlorosilane and the other high-boiling components, as well as the entrained fines; and a remainder product stream 16, containing the remaining small amount of vinyltrichlorosilane, which stream is passed to a brine-cooled cooling unit 17.

In the brine-cooled cooler 17, a light-boiling fraction 18 is separated out as a liquid comprised mostly of unconverted starting materials, plus a small amount of vinyltrichlorosilane. The unconverted starting materials may be reused by, e.g., putting fraction 18 back through reactor 1. The remaining gas stream 19 may be treated to remove the hydrogen chloride, e.g. by a customary water wash, and then vented to the atmosphere.

To improve the conversion without sacrificing the high selectivity, the inventive method may also be realized in a cascade of two or more successive fluidized beds.

The following Examples are offered for the purpose of further elucidating the invention, but do not limit the scope of the invention.

EXAMPLE 1

In a laboratory apparatus essentially corresponding to that illustrated in FIG. 2, vinyl chloride and trichlorosilane were reacted to form vinyltrichlorosilane, at the feed rates indicated in Table 1. The reactor 1 (comprised of stainless steel No. 1.4571) was 30 cm long, with inner diameter 16 mm and wall thickness 2.6 mm. The reactor 1 was electrically heated from the exterior. A diffusor-like gas inlet nozzle (not shown) was provided in the lower part of the reactor 1. When flow rates were sufficient, said nozzle produced thorough intermixing of the starting materials vinyl chloride 5 and trichlorosilane 6 prior to the feed through the stainless steel screen 4 and thence to the fluidized bed 2. Nitrogen 7 in the amounts given in Table 1 was introduced to the reactor 1 along with the trichlorosilane 6. The gas inlet nozzle was cooled with air in order to ensure that the starting materials did not reach reaction temperatures until they entered the fluidized bed and in order to ensure that the stainless steel screen 4 did not become clogged.

Silicon carbide with particle sizes in the range 400–500 micron or 500–630 micron was used as the inert fluidized be material. The respective mean particle sizes of these particle mixes were 450 and 565 micron, respectively. The mesh size of the stainless steel screen 4 was 300 micron. The rest height of the fluidized bed was 4 or 8 cm, as indicated in Table 1. The gaseous raw product in line 13 was cooled with air, to afford rapid cooling and suppression of subsequent reactions.

In a series of Experiments, the following parameters were varied as seen in Table 1: the feed rates of the starting materials, the ratio of nitrogen to the starting materials, the temperature, the rest height of the fluidized bed, and the particle size distribution. The composition of the product stream was determined by gas chromatographic analysis. The conversions and selectivities obtained presented in Table 2.

Symbols

The symbols used in the Tables and FIG. 2 are defined as follows:

| | |
|---|---|
| $d_p$ | Mean diameter of the particle mix |
| $H°$ | Rest height of the fluidized bed |
| VC | Vinyl chloride |
| TCS | Trichlorosilane |
| $N_2$ | Nitrogen |
| VTC | Vinyltrichlorosilane |
| TET | Tetrachlorosilane |
| UK1 | Unknown component 1 |
| UK2 | Unknown component 2 |
| ETCS | Ethyltrichlorosilane |
| HS | High-boiling components |
| LS | Low-boiling components. |

TABLE 1

| Experiment No. | $d_p$ μm | H° cm | Temp. °C. | Feed Stream (mol/hr) VC | TCS | $N_2$ | Product Stream (mol/hr) VTC | TET | UK1 | HS | UK2 | ETCS |
|---|---|---|---|---|---|---|---|---|---|---|---|---|
| 1 | 450 | 4 | 720 | 2.40 | 2.40 | 2.00 | 0.858 | 0.109 | 0.072 | 0.006 | 0.008 | 0.002 |
| 2 | 450 | 4 | 700 | 3.45 | 3.45 | 1.60 | 0.556 | 0.049 | 0.010 | 0.006 | 0.003 | 0.008 |
| 3 | 450 | 4 | 725 | 3.60 | 3.60 | 1.60 | 1.163 | 0.102 | 0.073 | 0.006 | 0.008 | 0.040 |
| 4 | 430 | 4 | 730 | 4.80 | 4.80 | 2.40 | 1.690 | 0.162 | 0.132 | 0.019 | 0.011 | 0.015 |
| 5 | 450 | 4 | 715 | 4.60 | 4.70 | 2.40 | 1.642 | 0.141 | 0.085 | 0.011 | 0.016 | 0.034 |
| 6 | 450 | 4 | 740 | 4.80 | 4.80 | 2.50 | 2.120 | 0.259 | 0.362 | 0.021 | 0.026 | 0.013 |
| 7 | 450 | 4 | 775 | 4.80 | 4.80 | 0.85 | 1.566 | 0.173 | 0.295 | 0.026 | 0.024 | 0.001 |
| 8 | 565 | 8 | 720 | 2.40 | 2.40 | 2.30 | 1.144 | 0.132 | 0.121 | 0.006 | 0.010 | 0.013 |
| 9 | 565 | 8 | 650 | 2.40 | 2.40 | 2.70 | 0.398 | 0.031 | 0.012 | 0.006 | 0.005 | 0.029 |

TABLE 2

| Experiment No. | Conversion with reference to VC; except that in the case of TET the conversion is with reference to TCS. | | | | | | Selectivity for VTC, with reference to VC |
|---|---|---|---|---|---|---|---|
| | VTC | TET | UK1 | HS | UK2 | ETCS | |
| 1 | 0.358 | 0.045 | 0.030 | 0.003 | 0.003 | 0.001 | 0.814 |
| 2 | 0.161 | 0.014 | 0.003 | 0.002 | 0.001 | 0.002 | 0.880 |
| 3 | 0.323 | 0.028 | 0.020 | 0.002 | 0.002 | 0.011 | 0.837 |
| 4 | 0.352 | 0.034 | 0.028 | 0.004 | 0.002 | 0.003 | 0.832 |
| 5 | 0.357 | 0.030 | 0.018 | 0.002 | 0.003 | 0.007 | 0.856 |
| 6 | 0.442 | 0.054 | 0.075 | 0.004 | 0.005 | 0.003 | 0.758 |
| 7 | 0.326 | 0.036 | 0.061 | 0.005 | 0.004 | 0.001 | 0.754 |
| 8 | 0.477 | 0.055 | 0.050 | 0.003 | 00.04 | 0.005 | 0.803 |
| 9 | 0.166 | 0.013 | 0.005 | 0.003 | 0.002 | 0.012 | 0.826 |

EXAMPLE 2

Vinyltrichlorosilane was produced on an industrial scale in a fluidized bed reactor with diameter 0.60 m, with the rest height of the fluidized bed being 0.30 m.

VC and TCS were fed to the reactor in a ratio of 1:3.5 by weight. The temperature was 700° C., the pressure 1 bar, the superficial velocity 0.74 m/sec, and the height of the expanded fluidized bed c. 2 m. Under these conditions, the limits of the particle sizes of the inert fluidized bed material were 120 micron (for non-entrainment) and 400 micron (for fluidizability). The reactor was capable of producing 155 tonne VTC/mo, at a conversion of 50% and a selectivity for VTC of 80% (with reference to the VC).

German Patent Applications 196 45 700.9 filed Nov. 6, 1996, and 197 27 576.1 filed Jun. 28, 1997, are incorporated herein by reference.

What is claimed as new and desired to be secured by Letters Patent of the United States is:

1. A method of manufacturing vinyltrichlorosilane comprising reacting vinyl chloride with trichlorosilane at 400°–850° C. in a fluidized bed.

2. The method according to claim 1, wherein the reaction is carried out at 550°–800° C.

3. The method according to claim 1, wherein that the fluidized bed material has a particle size in the range of 80–800 microns.

4. The method according to claim 3, wherein the fluidized bed material is comprised of silicon carbide.

5. The method according to claim 1, wherein the ratio of vinyl chloride to trichlorosilane is in the range of 1:2 to 1:4 by weight.

6. The method according to claim 1, wherein an inert gas is introduced to the fluidized bed in addition to the vinyl chloride and trichlorosilane.

7. The method according to claim 1, wherein the mean residence time of reactants in the fluidized bed is 0.1–0.2 sec.

8. The method according to claim 1, wherein the reaction is carried out in a cascade of successive fluidized beds.

* * * * *